United States Patent [19]

Nakao et al.

[11] Patent Number: 5,494,040
[45] Date of Patent: Feb. 27, 1996

[54] ULTRASONIC DIAGNOSIS DEVICE WITH BRIGHT POSITION-INDICATING LINE

[75] Inventors: Narutaka Nakao; Masahiro Hiruta, both of Kawasaki, Japan

[73] Assignee: Fujitsu Limited, Kawasaki, Japan

[21] Appl. No.: 281,999

[22] Filed: Jul. 29, 1994

[30] Foreign Application Priority Data

Aug. 25, 1993 [JP] Japan ................................... 5-210312

[51] Int. Cl.⁶ .................................................. A61B 8/12
[52] U.S. Cl. ....................................................... 128/662.06
[58] Field of Search ........................ 128/660.09, 660.10, 128/660.08, 661.01, 662.06

[56] References Cited

U.S. PATENT DOCUMENTS 5,207,225  5/1993  Oaks et al. ........................... 128/662.06
5,257,628  11/1993  Ishiguro et al. ..................... 128/660.09

*Primary Examiner*—George Manuel
*Attorney, Agent, or Firm*—Staas & Halsey

[57] ABSTRACT

An ultrasonic diagnosis device comprising a probe having an ultrasonic sensor rotatable about a central axis thereof. The sensor is adapted to carry out ultrasonic sector scanning. The device also includes a display for producing a sectional image of a portion of a patient. A bright line corresponding to the central axis of the sensor is produced together with the sectional image on the display. A first sectional image is produced on the display when the sensor is in a first rotational position. The bright line is then produced over the sectional image, and the position of the sensor is adjusted so that the bright line passes through the center of an object in the image. The sensor is then moved to a second rotational position, and a second sectional image is produced on the display.

6 Claims, 6 Drawing Sheets

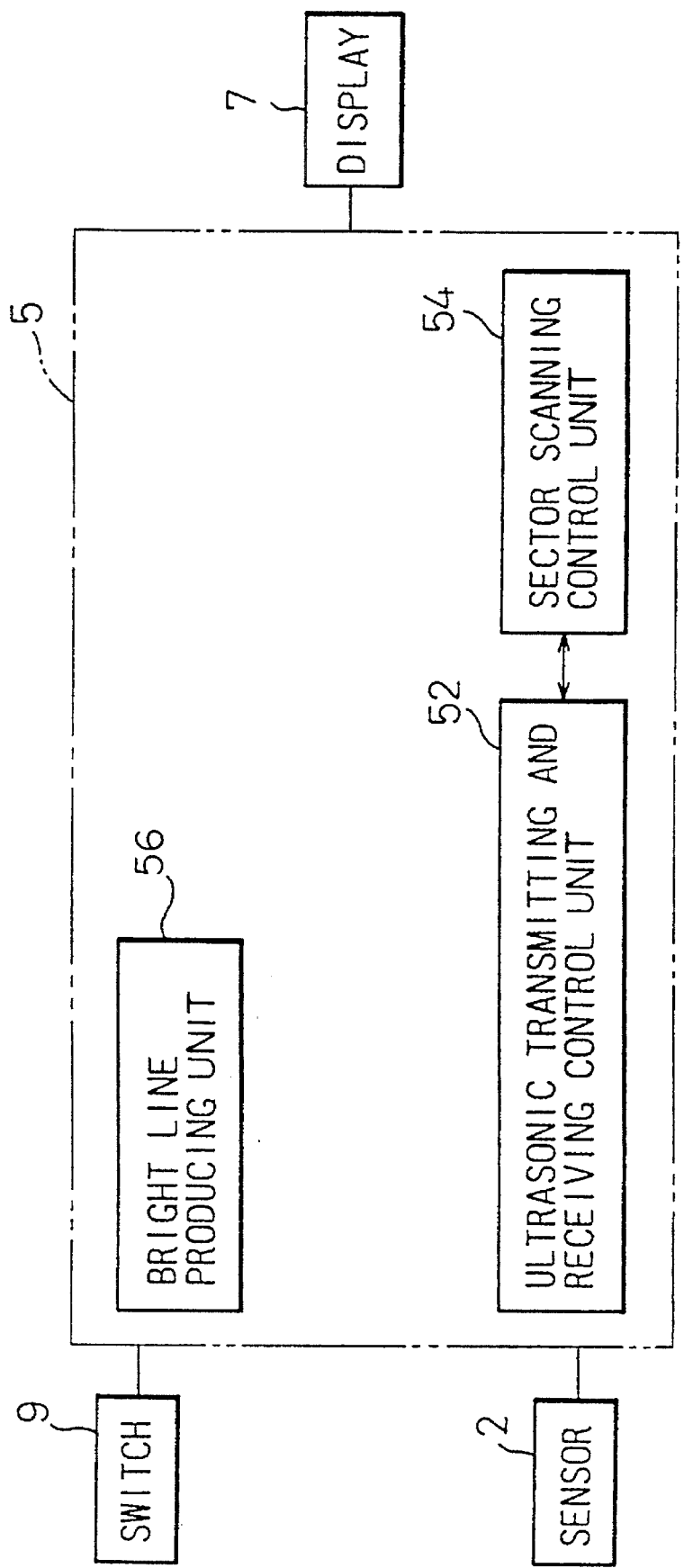

ULTRASONIC DIAGNOSIS DEVICE WITH BRIGHT POSITION-INDICATING LINE

BACKGROUND OF THE INVENTION

1. Field of the Invention

The present invention relates to an ultrasonic diagnosis device used for medical purposes.

2. Description of the Related Art

For use in medical diagnosis, an ultrasonic diagnosis probe having an ultrasonic sensor therein has been developed. The ultrasonic diagnosis probe is used on the surface of the body, and also in body cavities. In a trans-esophageal echo cardiograph, for example, an ultrasonic sectional image (tomograph) of an affected portion of a patient is made by inserting the probe into the esophagus so that the probe reaches the desired position in the body cavity and by carrying out sector scanning using a sensor which transmits ultrasound and receives reflected ultrasound (the echo signals). The echo signals are changed to brightness signals to produce on the display an image of the affected portion of the patient.

The ultrasonic sensor comprises an array of piezoelectric elements, The scanning is carried out in the direction of the array of piezoelectric elements. Therefore, the scanning direction is constant, and the obtained sectional image exists in a fixed plane only, and lacks flexibility.

To overcome this problem, an ultrasonic diagnosis device has been proposed in which an ultrasonic sensor is rotatably arranged, in a probe, about a central axis of the sensor extending perpendicular to the ultrasonic transmitting and receiving surface of the sensor. However, the conventional ultrasonic diagnosis device requires a complex operation, and many operating elements are necessary to produce an image. Therefore, it is difficult to easily obtain a sectional image of the object at exactly the desired position.

SUMMARY OF THE INVENTION

The object of the present invention is to solve the above described problems and to provide an ultrasonic diagnosis device which can be easily operated and by which it is possible to obtain a sectional image at exactly the desired position.

According to the present invention, an ultrasonic diagnosis device is provided. The ultrasonic diagnosis device of the present invention comprises a control unit, a probe having a first end operably connected to the control unit and a second end having an ultrasonic sensor arranged therein for ultrasonic sector scanning, the sensor having an ultrasonic transmitting and receiving surface and being rotatable relative to the probe about a central axis of the sensor extending perpendicular to the ultrasonic transmitting and receiving surface, a unit rotationally moving the sensor relative to the probe about said central axis by a desired angle, a display for producing a sectional image of an object obtained by the sector scanning of the sensor, and a unit producing a bright line corresponding to the central axis of the sensor together with the sectional image of the object in the display.

With this arrangement, the ultrasonic probe can be inserted in the body cavity or in the blood vessel and a short axis (transverse) image of a desired position of a person can be first obtained. The short axis image is appropriately produced on the display. A bright line corresponding to the central axis of the sensor is then produced over the short axis image on the display, and the probe is adjusted so that the center of the short axis image coincides with the bright line, resulting that the sensor being located at the central line of the long axis of the target portion of the body being diagnosed, The sensor is then rotated by 90 degrees by the unit. It is then possible to exactly make the desired long axis image at the portion to be diagnosed in the longitudinal cross section.

BRIEF DESCRIPTION OF THE DRAWINGS

The present invention will become more apparent from the following description of the preferred embodiment, with reference to the accompanying drawings, in which:

FIG. 6 is a block diagram of the controller of FIG. 1;

DESCRIPTION OF THE PREFERRED EMBODIMENTS

Figure 1:
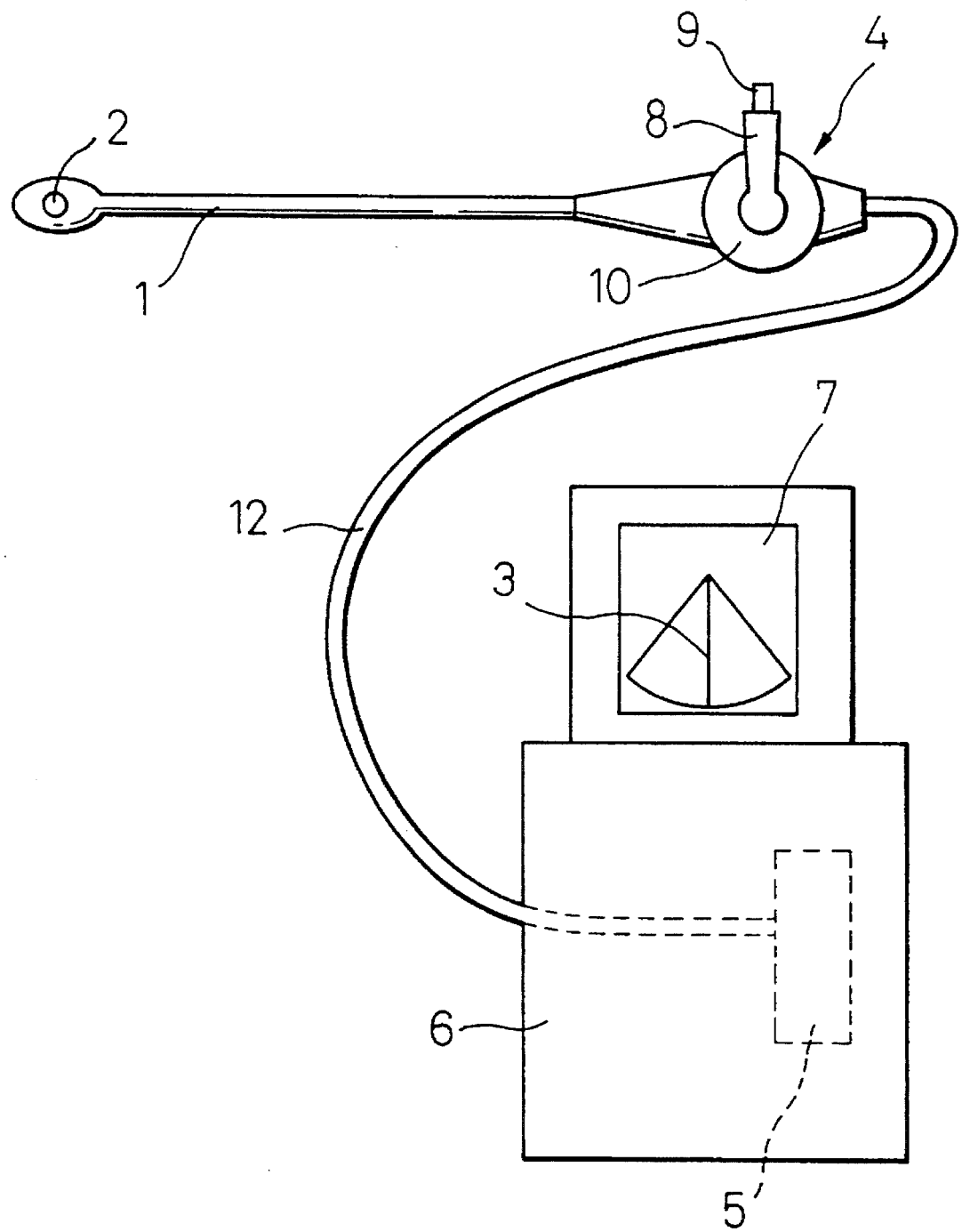
FIG. 1 is a diagrammatic view of an ultrasonic diagnosis device according to the embodiment of the present invention.

FIG. 1 shows, in principle, an ultrasonic diagnosis device according to the present invention. FIGS. 2 to 5 show the details of a probe and an ultrasonic sensor. The ultrasonic diagnosis device comprises an ultrasonic probe 1, a control unit 6 having a controller 5, and a display 7. A manual operating unit 4 is attached to the proximal end of the probe 1 to facilitate the handling of the probe 1. The proximal end of the probe 1 is connected to the control unit 6 via a cable 12. The manual operating unit 4 includes a handle 8 and a switch 9, which are described later. The handle 8 and the switch 9 are arranged close to each other.

The ultrasonic probe 1 is flexible but has sufficient rigidity to be rotated by a predetermined angle when the probe 1 is inserted in the esophagus. The free end portion thereof can be bent by operating a knob 10 in the manual operating unit 4, as shown by the arrow B in FIG. 3. The detailed description of the bending mechanism is omitted here.

Figure 4:
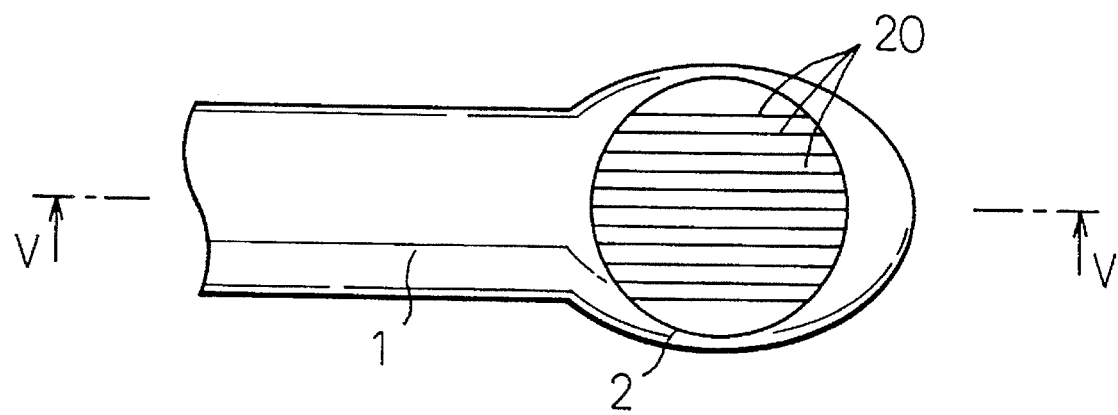
FIG. 4 is an enlarged plan view of a portion of the probe of FIGS. 1 and 2.
Figure 5:
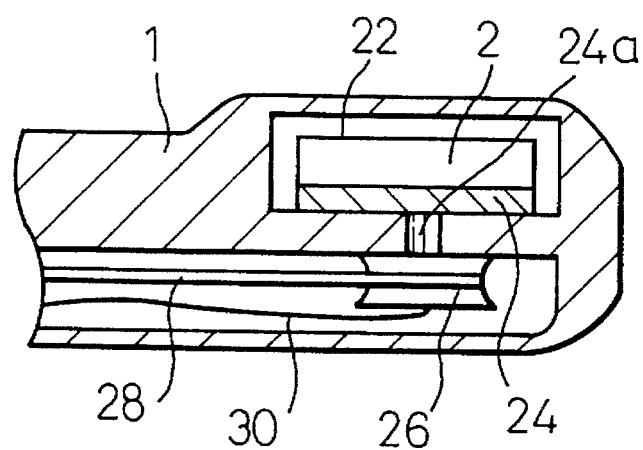
FIG. 5 is a cross-sectional view of the probe of FIG. 4 taken along the line V—V in FIG. 4.

An ultrasonic sensor 2 is arranged in the distal end of the probe 1. The ultrasonic sensor 2 comprises an array of piezoelectric elements 20 adapted to electronically carry out an ultrasonic sector scanning, as shown in FIG. 4. The sensor 2 has an ultrasonic transmitting and receiving surface 22. The sensor 2 is rotatable about a central axis 3a of the sensor 2 extending perpendicular to the ultrasonic transmitting and receiving surface 22, as shown by the arrow A in FIG. 2.

The handle 8 in the manual operating unit 4 causes the sensor 2 to rotate about the central axis 3a by a desired degree. To this end, the sensor 2 is fixed to a disk 24 which has a shaft 24a standing at the center of the lower surface of the rotor disk 24. The shaft 24a passes through the wall of the probe 1. A pulley 26 is fixed to the shaft 24a. A wire 28 is wound on the pulley 26 and connected to the handle 8 so that the sensor 2 can be rotated by the operation of the handle 8. The shaft 24a and the pulley 26 have respective through holes (not shown) through which a cable 30 extends to connect the piezoelectric elements 20 of the sensor 2 to the external electric element. Alternatively, it is possible to arrange an actuator such as an electric motor near the sensor 2 to rotationally move the sensor 2. In this case, the handle may be replaced by a unit controlling the actuator.

FIG. 6 is a block diagram of the controller 5 of FIG. 1. The controller 5 comprises an ultrasonic transmitting and receiving control unit 52 and a sector scanning control unit 54. The ultrasonic transmitting and receiving control unit 52 allows the sensor 2 to transmit ultrasound towards an object and to receive the reflected ultrasound. The sector scanning control unit 54 cooperates with the ultrasonic transmitting and receiving control unit 52 to scan the piezoelectric elements 20 to thereby produce an image on the display 7. Sector scanning is well known and the detailed explanation thereof is omitted here.

The controller 5 also comprises a bright line producing unit 56 for producing a bright line 3 (FIG. 1) corresponding to the central axis 3a of the sensor 2 together with the sectional image on the display 7. The bright line producing unit 56 is enabled at a desired time, depending on the operation of the switch 9 in the manual operating unit 4, such that the bright line 3 appears when the switch 9 is pushed and the bright line 3 is eliminated when the switch 9 is released. The image appears on the display 7 in the form of a sector having a center line. The bright line 3 passes through the center line of the sector, as shown in FIG. 1.

Figure 2:
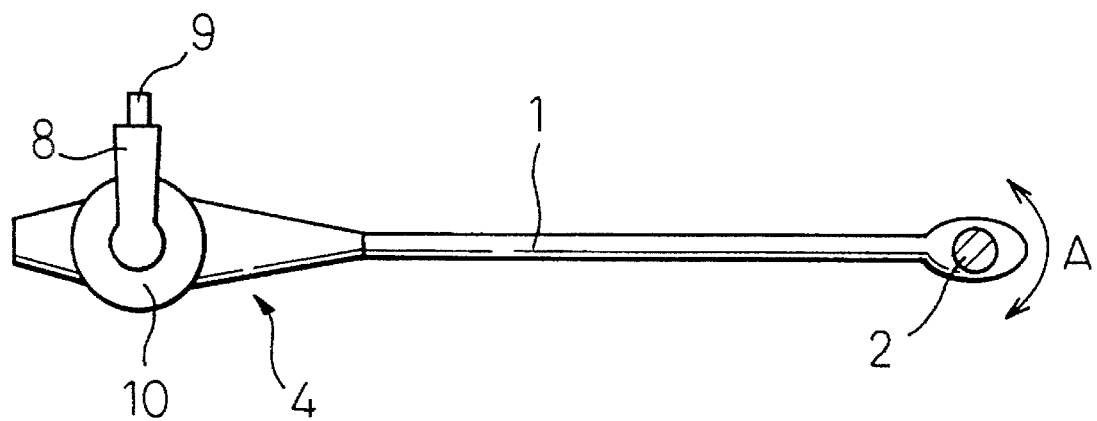
FIG. 2 is a plan view of the ultrasonic probe of FIG. 1.
Figure 3:
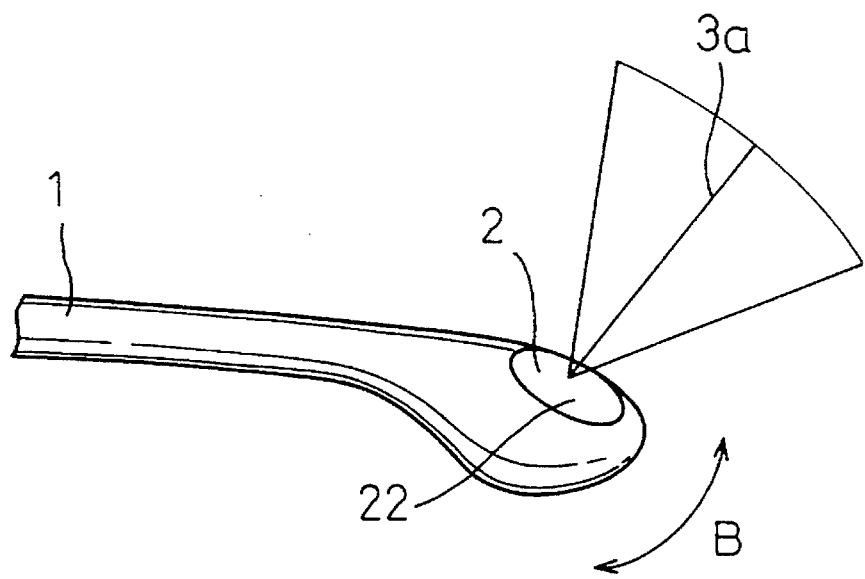
FIG. 3 is a side view of a portion of the probe of FIGS. 1 and 2.

In the embodiment shown in FIGS. 1 and 2, the manual operating unit 4 including the handle 8 and the switch 9 is arranged on the proximal end of the probe 1. However, it is possible, for example, to arrange the manual operating unit 4 on the control unit 6.

Figure 7A:
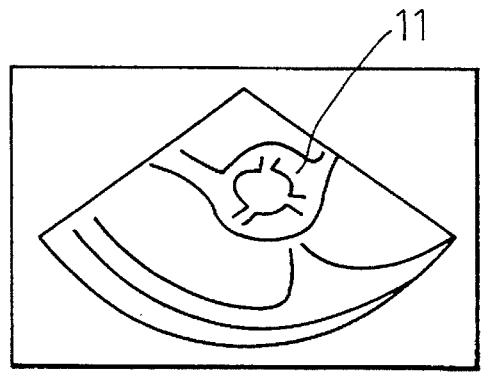
FIGS. 7A to 7D are views illustrating the operation of the ultrasonic diagnosis device of FIGS. 1 to 6.

In operation, the imaging sequence is described with reference to FIGS. 7A to 7D, and 8, by way of an example where a valve of the heart such as aortic valve is observed by the probe 1. The probe 1 is inserted in the esophagus so that the sensor 2 reaches a desired position (step 60) in the esophagus near the heart, and the knob 10 in the manual operating unit 4 is operated to bend the end portion of the probe 1 (step 61). The handle 8 is operated to rotate the sensor 2 relative to the probe 1. The probe itself is also rotated, in order to locate a valve to be diagnosed (step 62). The sector scanning is carried out and a sectional image of the object, i.e., a cylindrical tube (blood vessel) 11 having a valve is produced in the display 7, as shown in FIG. 7A. This sectional image is called a short axis (transverse) image of the cylindrical tube 11.

Figure 7B:
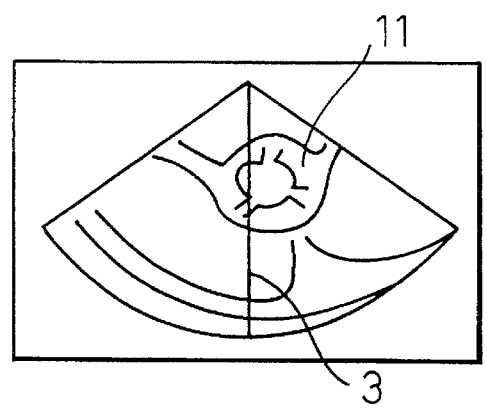
Figure 7C:
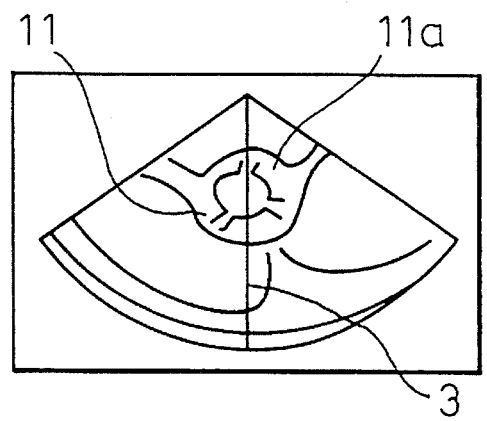

The switch 9 is then operated to produce the bright line 3 over the image of the cylindrical tube 11 in the display 7 (step 63), in order to move the obtained short axis image to the center of the screen. This condition is shown in FIG. 7B. The bright line 3 corresponds to the central axis 3a of the sensor 2. The probe 1 itself is rotated to adjust the position of the sensor 2 so that the bright line 3 passes through the center of the cylindrical tube 11 (step 64). FIG. 7C shows this adjusted position. A valve 11a can be seen.

Figure 7D:
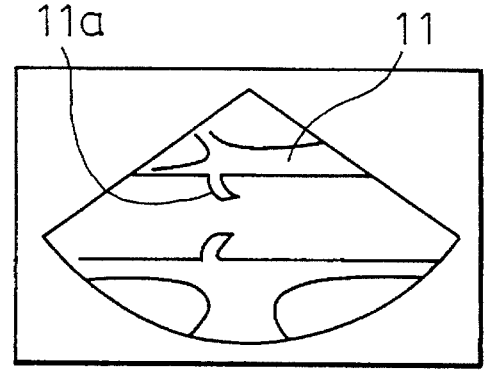
Figure 8:
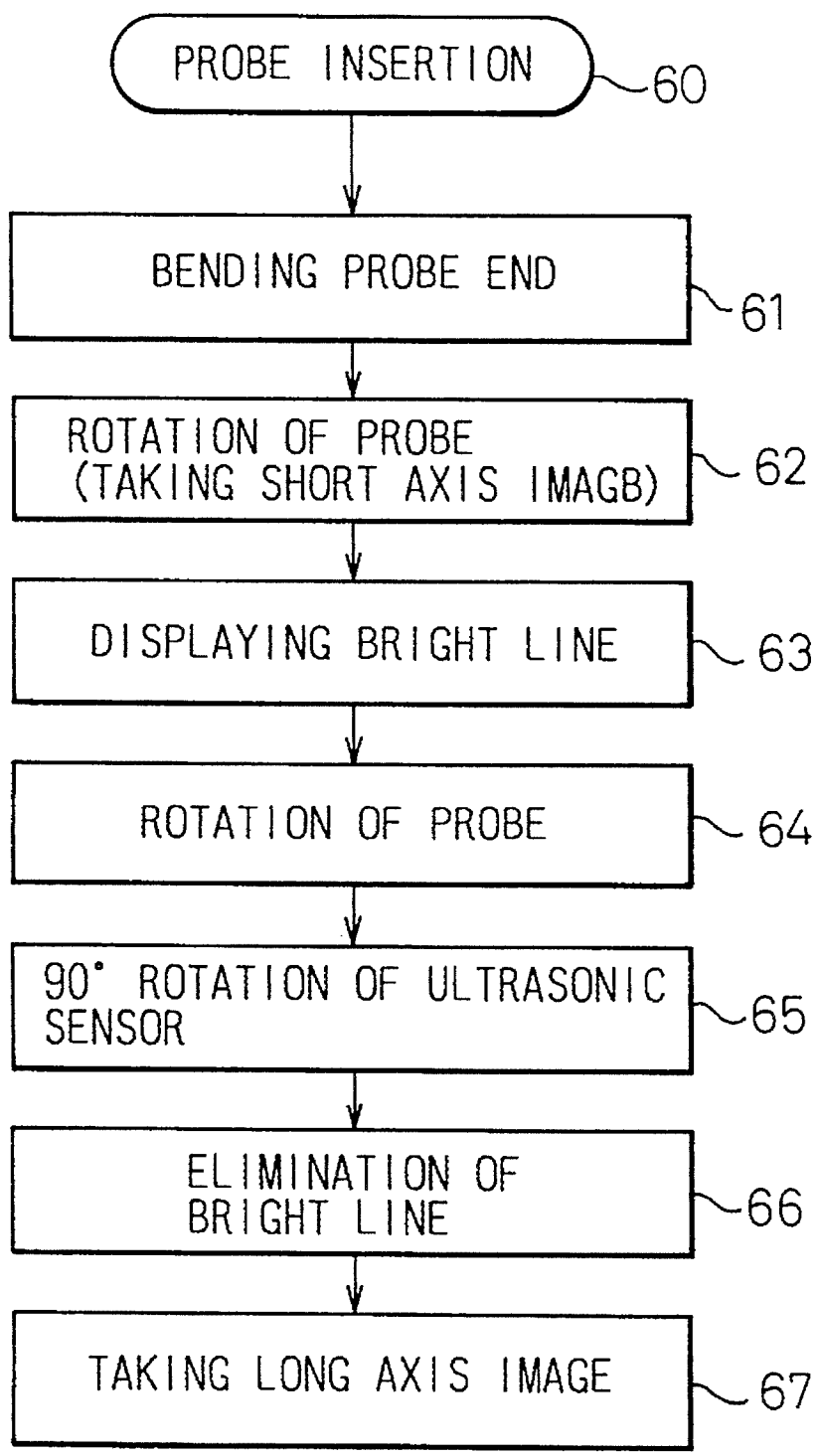
FIG. 8 is a flow chart of the imaging method of the present invention.

In this condition, the sensor 2 is in such a position that the bright line 3 passes through the center of the cylindrical tube 11 and the scanning direction is perpendicular to the cylindrical tube 11. The sensor 2 is then rotated by 90 degrees, about the central axis 3a, from the above described position, with the being that the scanning direction only is rotated by 90 degrees (step 65). The bright line 3 is then eliminated (step 66), and the longitudinal cross-sectional image of the cylindrical tube 11 including the valve 11a is obtained (step 67). FIG. 7D shows this condition, and this image is called a long axis image of the cylindrical tube 11.

The probe 1 is bendable in the above described embodiment, but it will be appreciated that the probe 1 is not necessarily bendable. If the adjustment of the front viewing field is not necessary, the feature of the present invention can be established even if with the probe 1 is not bendable.

It is also possible to omit the switch 9 and to normally produce the bright line 3 in the display 7 while the diagnosis is carried out.

As explained above, according to the present invention, it is possible to easily and exactly obtain a tomograph of a desired portion of a patient, while monitoring the image in the display.

We claim:

1. An ultrasonic diagnosis device comprising:

a control unit;

a probe comprising a first end operably connected to the control unit and a second end comprising an ultrasonic sensor arranged therein for ultrasonic sector scanning, the ultrasonic sensor comprising an ultrasonic transmitting and receiving surface and being rotatable relative to the probe about a central axis of the sensor extending perpendicular to the ultrasonic transmitting and receiving surface;

means for rotationally moving the sensor relative to the probe about said central axis by a desired angle;

a display producing an image of an object obtained by the sector scanning of the sensor; and means for producing a bright line corresponding to the central axis of the sensor, together with the image of the object, on the display, wherein the bright line is at a fixed position on the display and superposed on the image of the object.

2. An ultrasonic diagnosis device according to claim 1, wherein said sensor comprises an array of piezoelectric elements.

3. An ultrasonic diagnosis device according to claim 1, wherein the image appears in the display in the form of a sector having a center line, and said bright line appears on the center line of the sector.

4. An ultrasonic diagnosis device according to claim 1, wherein said probe is flexible.

5. An ultrasonic diagnosis device comprising:

a control unit;

a probe comprising a first end operably connected to the control unit and a second end comprising an ultrasonic sensor arranged therein for ultrasonic sector scanning, the ultrasonic sensor comprising an ultrasonic transmitting and receiving surface and being rotatable relative to the probe about a central axis of the sensor extending perpendicular to the ultrasonic transmitting and receiving surface;

means for rotationally moving the sensor relative to the probe about said central axis by a desired angle;

a display producing an image of an object obtained by the sector scanning of the sensor; and means for producing a bright line corresponding to the central axis of the sensor together with the image of the object on the display, wherein said means for producing the bright line is arranged such that the bright line one of appears and is eliminated, depending on a signal from a manual switch.

6. An ultrasonic diagnosis device according to claim 5, further comprising a cable, wherein the first end of the probe comprises a manual unit comprising said moving means and said manual switch, the first end of the probe being connected to the control unit via the cable.

* * * * *

UNITED STATES PATENT AND TRADEMARK OFFICE
CERTIFICATE OF CORRECTION

PATENT NO. : 5,494,040
DATED : February 27, 1996
INVENTOR(S) : Narutaka NAKAO et al.

It is certified that error appears in the above-indentified patent and that said Letters Patent is hereby corrected as shown below:

Column 1, line 26, change "," to --.--.

Column 2, line 3, change "that" to --in--;

line 5, after "the" (2nd occurrence) insert --moving--.

Signed and Sealed this

Eighteenth Day of June, 1996

*Attest:*

BRUCE LEHMAN

*Attesting Officer*  *Commissioner of Patents and Trademarks*